US010241007B2

United States Patent
Martucci et al.

(10) Patent No.: US 10,241,007 B2
(45) Date of Patent: Mar. 26, 2019

(54) SYSTEM AND METHOD FOR THE CALCULATION OF A FUEL LACQUER INDEX

(71) Applicant: UNITED TECHNOLOGIES CORPORATION, Hartford, CT (US)

(72) Inventors: Angelo Martucci, Bloomfield, CT (US); William Donat, Manchester, CT (US); Amy Grace, Ellington, CT (US); Eric Hettler, Rochester, NY (US); Kevin McCormick, Auburn, NY (US); Kevin Gibbons, Torrington, CT (US); Haralambos Cordatos, Colchester, CT (US); Christopher Mazella, West Hartford, CT (US)

(73) Assignee: United Technologies Corporation, Farmington, CT (US)

( * ) Notice: Subject to any disclaimer, the term of this patent is extended or adjusted under 35 U.S.C. 154(b) by 371 days.

(21) Appl. No.: 15/018,651

(22) Filed: Feb. 8, 2016

(65) Prior Publication Data

US 2017/0227425 A1  Aug. 10, 2017

(51) Int. Cl.
| | | |
|---|---|---|
| *G01M 15/14* | (2006.01) | |
| *F02C 7/22* | (2006.01) | |
| *G01N 33/22* | (2006.01) | |
| *F01D 21/00* | (2006.01) | |

(52) U.S. Cl.
CPC .......... *G01M 15/14* (2013.01); *F01D 21/003* (2013.01); *F02C 7/222* (2013.01); *G01N 33/22* (2013.01)

(58) Field of Classification Search
CPC ........ G01M 15/14; F02C 7/222; G01N 33/22; F01D 21/003
See application file for complete search history.

(56) References Cited

U.S. PATENT DOCUMENTS

| | | | | |
|---|---|---|---|---|
| 2007/0260374 A1* | 11/2007 | Morrison | ................ | F02D 41/22 701/99 |
| 2010/0064657 A1* | 3/2010 | Mahoney | ................ | F02C 7/236 60/39.281 |
| 2017/0051682 A1* | 2/2017 | Simmons | .................. | F02C 7/22 |

FOREIGN PATENT DOCUMENTS

EP    1128058    8/2001

OTHER PUBLICATIONS

Øyvind Buhaug.,"Deposit formation on cylinder liner surfaces in medium-speed engines"., Faculty of Engineering Science and Technology Norwegian University of Science and Technology., Trondheim, Sep. 15, 2003.*
EP Search Report dated Jul. 21, 2017 in EP Application No. 17155065.0.

* cited by examiner

*Primary Examiner* — Yoshihisa Ishizuka
(74) *Attorney, Agent, or Firm* — Snell & Wilmer, L.L.P (57) ABSTRACT

A system and method for the calculation of a fuel lacquer index using environmental monitoring is disclosed. The system and method may comprise: capturing a fuel temperature data; determining a fuel quality rating; calculating a volumetric fuel flow; calculating a fuel filter differential pressure; and calculating a fuel lacquer index. The fuel lacquer index may be calculated as a percentage value based upon the fuel temperature data, the fuel quality rating, the volumetric fuel flow, and the fuel filter differential pressure.

20 Claims, 4 Drawing Sheets

SYSTEM AND METHOD FOR THE CALCULATION OF A FUEL LACQUER INDEX

FIELD

The present disclosure relates generally to gas turbine engines, and more specifically, to systems and methods for monitoring the health of fuel systems.

BACKGROUND

Engine components and fittings may be subjected to relatively high temperatures during operation. As fuel operating temperature and flow rate rise during operation, fuel lacquering may occur. Fuel lacquering may cause hardened and/or sticky particulate to be separated from the liquid phase of the fuel and become deposited on components within fuel flow paths of the fuel system. As fuel lacquering particulates begin to build, it may cause undesirable effects such as blocked passageways and filters. Moreover, excessive heating, cyclic loading, and other harsh conditions of engine components may lead to degradation of component health.

SUMMARY

Systems and methods for monitoring the health of fuel actuation systems are described herein. In various embodiments, a method for the calculation of a fuel lacquer index ("FLI") is disclosed. The method may comprise capturing a fuel temperature data. The method may comprise determining a fuel quality rating. The method may comprise calculating a volumetric fuel flow. The method may comprise calculating a fuel filter differential pressure. The fuel lacquer index may be calculated based on the fuel temperature data, the fuel quality rating, the volumetric fuel flow, and the fuel filter differential pressure.

In various embodiments, the method may further comprise generating a low warning in response to the fuel lacquer index being greater than 60%, a fault warning in response to the fuel lacquer index being greater than 75%, and/or a service warning in response to the fuel lacquer index being greater than 85%. The fuel temperature data, the fuel quality rating, the volumetric fuel flow, and the fuel filter differential pressure may also be stored in an FLI database. The fuel quality rating may comprise at least one of a low fuel quality rating, a medium fuel quality rating, or a high fuel quality rating. The volumetric fuel flow may be calculated through the use of a volumetric fuel flow model. The volumetric fuel flow model may be based upon a position of a fuel control actuator.

In various embodiments, a system may comprise a fuel temperature sensor, a fuel filter pressure sensor, and a processor. The fuel temperature sensor may be configured to monitor the temperature of a fuel. The fuel filter pressure sensor may be configured to monitor a fuel filter. The processor may be configured to perform operations comprising: capturing a fuel temperature data; determining a fuel quality rating; calculating a volumetric fuel flow; calculating a fuel filter differential pressure; and calculating a fuel lacquer index. The fuel lacquer index may comprise a calculation based on the fuel temperature data, the fuel quality rating, the volumetric fuel flow, and the fuel filter differential pressure.

In various embodiments, the system may further comprise operations comprising: generating a low warning in response to the fuel lacquer index being greater than 60%, a fault warning in response to the fuel lacquer index being greater than 75%, and/or a service warning in response to the fuel lacquer index being greater than 85%. The fuel temperature data, the fuel quality rating, the volumetric fuel flow, and the fuel filter differential pressure may also be stored in an FLI database. The fuel quality rating may comprise at least one of a low fuel quality rating, a medium fuel quality rating, or a high fuel quality rating. The volumetric fuel flow may be calculated through the use of a volumetric fuel flow model. The volumetric fuel flow model may be based upon a position of a fuel control actuator.

In various embodiments, an article of manufacture is disclosed. The article of manufacture may include a tangible, non-transitory computer-readable storage medium having instructions stored thereon that, in response to execution by a processor, cause the processor to perform operations. The operations may comprise: capturing a fuel temperature data; determining a fuel quality rating; calculating a volumetric fuel flow; calculating a fuel filter differential pressure; and calculating a fuel lacquer index. The fuel lacquer index may be calculated based on the fuel temperature data, the fuel quality rating, the volumetric fuel flow, and the fuel filter differential pressure.

In various embodiments, the article of manufacture may further comprise operations comprising: generating a low warning in response to the fuel lacquer index being greater than 60%, a fault warning in response to the fuel lacquer index being greater than 75%, and/or a service warning in response to the fuel lacquer index being greater than 85%. The fuel temperature data, the fuel quality rating, the volumetric fuel flow, and the fuel filter differential pressure may also be stored in a FLI database. The fuel quality rating may comprise at least one of a low fuel quality rating, a medium fuel quality rating, or a high fuel quality rating.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the following illustrative figures.

Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the disclosures, it should be understood that other embodiments may be realized and that logical changes and adaptations in design and construction may be made in accordance with this disclosure and the teachings herein. Thus, the detailed description herein is presented for purposes of illustration only and not of limitation.

The scope of the disclosure is defined by the appended claims and their legal equivalents rather than by merely the examples described. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts but not necessarily to denote the same or different materials.

Computer-based system program instructions and/or processor instructions may be loaded onto a tangible, non-transitory computer readable medium having instructions stored thereon that, in response to execution by a processor, cause the processor to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In re Nuijten to fall outside the scope of patentable subject matter under 35 U.S.C. § 101.

Figure 1:
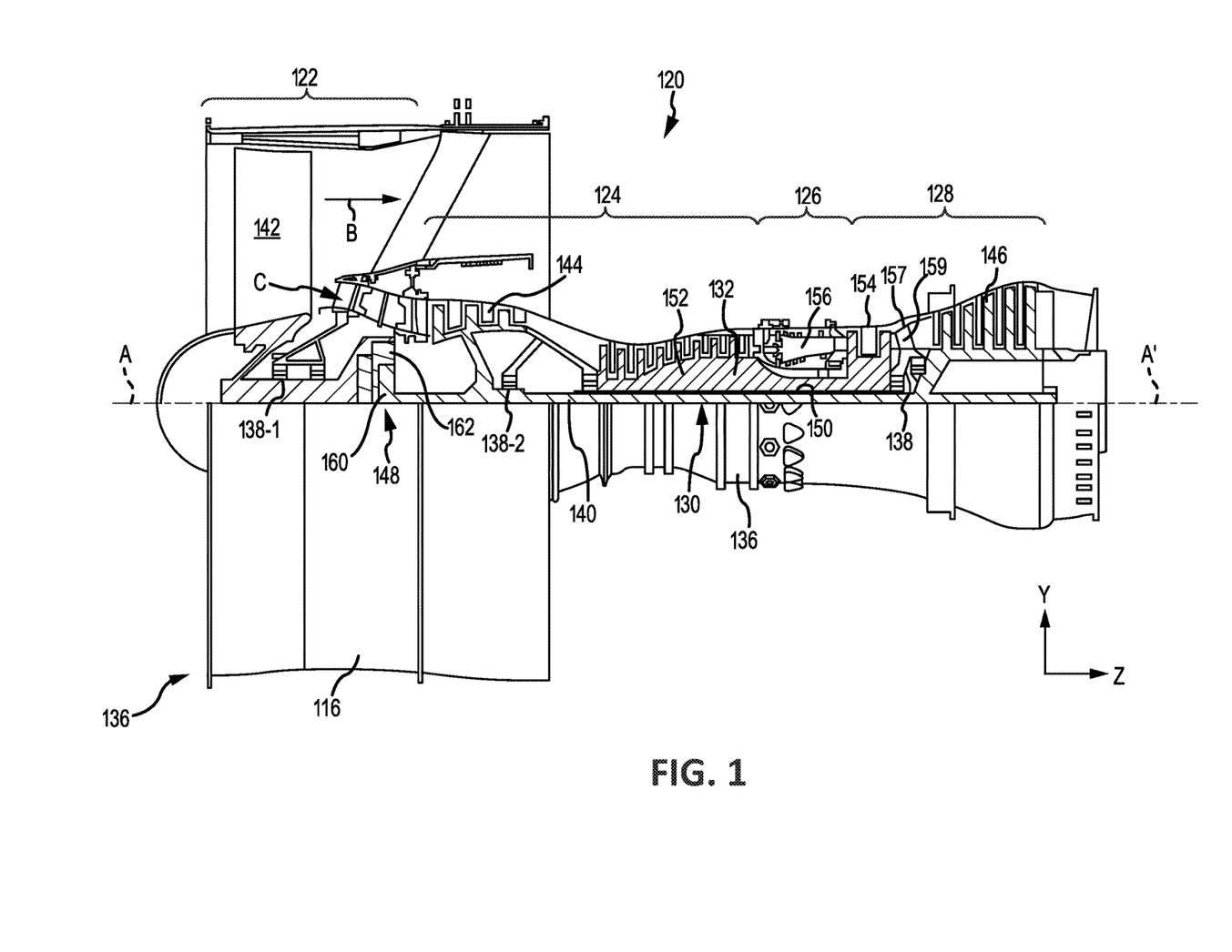
FIG. 1 illustrates a gas turbine engine, in accordance with various embodiments.

In various embodiments, and with reference to FIG. 1, a gas turbine engine 120 is disclosed. Gas turbine engine 120 may comprise a two-spool turbofan that generally incorporates a fan section 122, a compressor section 124, a combustor section 126, and a turbine section 128. Gas turbine engine 120 may also comprise, for example, an augmenter section, and/or any other suitable system, section, or feature. In operation, fan section 122 may drive air along a bypass flow-path B, while compressor section 124 may further drive air along a core flow-path C for compression and communication into combustor section 125, before expansion through turbine section 128. FIG. 1 provides a general understanding of the sections in a gas turbine engine, and is not intended to limit the disclosure. The present disclosure may extend to all types of applications and to all types of turbine engines, including, for example, turbofan gas turbine engines and turbojet engines.

In various embodiments, gas turbine engine 120 may comprise a low speed spool 130 and a high speed spool 132 mounted for rotation about an engine central longitudinal axis A-A' relative to an engine static structure 136 via one or more bearing systems 138 (shown as, for example, bearing system 138-1 and bearing system 138-2 in FIG. 1). It should be understood that various bearing systems 138 at various locations may alternatively or additionally be provided, including, for example, bearing system 138, bearing system 138-1, and/or bearing system 138-2.

In various embodiments, low speed spool 130 may comprise an inner shaft 140 that interconnects a fan 142, a low pressure (or first) compressor section 144, and a low pressure (or first) turbine section 146. Inner shaft 140 may be connected to fan 142 through a geared architecture 148 that can drive fan 142 at a lower speed than low speed spool 130. Geared architecture 148 may comprise a gear assembly 160 enclosed within a gear housing 162. Gear assembly 160 may couple inner shaft 140 to a rotating fan structure. High speed spool 132 may comprise an outer shaft 150 that interconnects a high pressure compressor ("HPC") 152 (e.g., a second compressor section) and high pressure (or second) turbine section 154. A combustor 156 may be located between HPC 152 and high pressure turbine 154. A mid-turbine frame 157 of engine static structure 136 may be located generally between high pressure turbine 154 and low pressure turbine 146. Mid-turbine frame 157 may support one or more bearing systems 138 in turbine section 128. Inner shaft 140 and outer shaft 150 may be concentric and may rotate via bearing systems 138 about engine central longitudinal axis A-A'. As used herein, a "high pressure" compressor and/or turbine may experience a higher pressure than a corresponding "low pressure" compressor and/or turbine.

In various embodiments, the air along core airflow C may be compressed by low pressure compressor 144 and HPC 152, mixed and burned with fuel in combustor 156, and expanded over high pressure turbine 154 and low pressure turbine 146. Mid-turbine frame 157 may comprise airfoils 159 located in core airflow path C. Low pressure turbine 146 and high pressure turbine 154 may rotationally drive low speed spool 130 and high speed spool 132, respectively, in response to the expansion.

Figure 2:
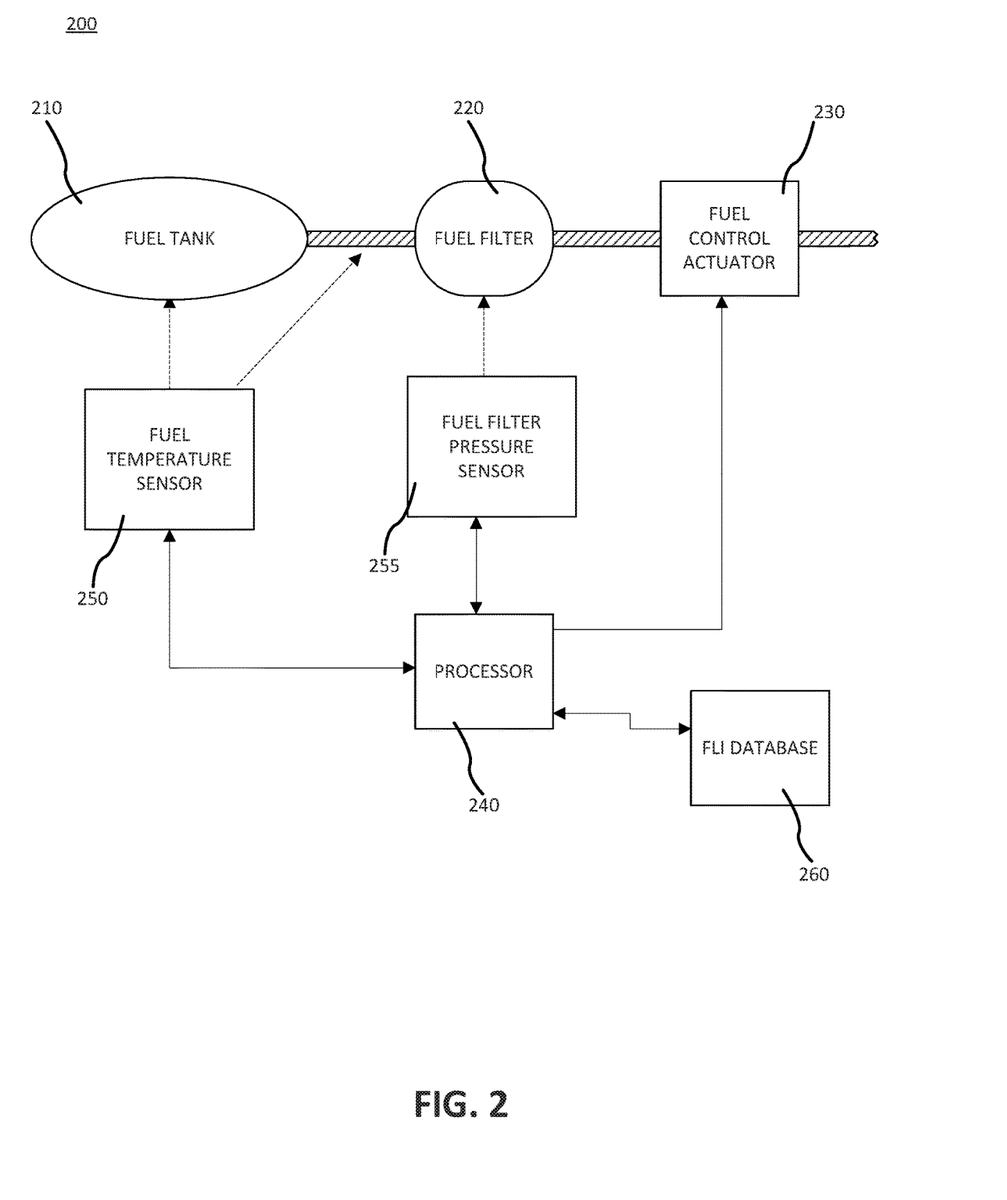
FIG. 2 illustrates a block diagram of a fuel system for a gas turbine engine, in accordance with various embodiments.

In various embodiments, and with reference to FIG. 2, a fuel system 200 is disclosed.

Gas turbine engine 120 may be operatively connected to fuel system 200. Gas turbine engine 120 may be operatively connected to fuel system 200 using any suitable method disclosed herein and/or known in the art. Fuel system 200 may be configured to fluidly provide fuel to gas turbine engine 120. In various embodiments, fuel system 200 may comprise a fuel tank 210, a fuel filter 220, a fuel control actuator 230, a processor 240, a fuel temperature sensor 250, a fuel filter pressure sensor 255, and a fuel lacquer index ("FLI") database 260. Fuel may flow in fuel system 200 from fuel tank 210, through fuel filter 220, and to fuel control actuator 230 before dispersal where desired. Fuel system 200 may also generally comprise any other suitable fuel system component, module, pump, actuator, valve, meter, nozzle, and/or the like.

In various embodiments, fuel tank 210 may be configured to store fuel for fuel system 200. Fuel tank 210 may comprise any suitable type of storage component capable of storing fuel for fuel system 200. Fuel tank 210 may be in fluid communication with and/or operatively coupled to fuel filter 220. Fuel tank 210 may be in fluid communication or operatively coupled using any suitable method described herein and/or known in the art, such as, for example, through the use of a pipe.

In various embodiments, fuel filter 220 may be configured as a mechanism to filter fuel flowing from fuel tank 210 and through the rest of fuel system 200. Fuel filter 220 may comprise any suitable type of filter capable of filtering fuel through a fuel system. In various embodiments, fuel filter 220 may be coupled to another fuel system component, such as, for example, a fuel pump. Fuel filter 220 may be configured to receive fuel from fuel tank 210, and fluidly pass the fuel to fuel control actuator 230. In this regard, fuel filter 220 may be in fluid communication with and/or operatively coupled to fuel tank 210 and fuel control actuator 230. Fuel filter 220 may be in fluid communication or operatively coupled using any suitable method described herein and/or known in the art, such as, for example, through the use of a pipe.

In various embodiments, fuel control actuator 230 may be configured to control fuel flow through fuel system 200. Fuel control actuator 230 may comprise any suitable type of actuator capable of controlling fuel flow. Moreover, fuel control actuator 230 may comprise any number of actuators, and may comprise screens, valves, and/or any other suitable components. Fuel control actuator 230 may control fuel flow by opening and closing valves to direct the flow of fuel through fuel system 200. Fuel control actuator 230 may be configured to receive fuel from fuel tank 220, through fuel filter 220, and fluidly pass the fuel through fuel system 200. In this regard, fuel control actuator 230 may be in fluid communication with and/or operatively coupled to fuel filter 220. Fluid control actuator 230 may be in fluid communication or operatively coupled using any suitable method described herein and/or known in the art, such as, for example, through the use of a pipe.

In various embodiments, processor 240 may comprise any suitable processor capable of sending and receiving data, and performing operations. Processor 240 may be configured to perform the calculations associated with monitoring and calculating the fuel lacquer index. Processor 240 may be located onboard an aircraft, and/or located externally from an aircraft. In this regard, processor 240 may be located within the aircraft's full authority digital engine control ("FADEC"), electronic engine control ("EEC") and/or located within the aircraft's health monitoring systems. Processor 240 may also be located off-board the aircraft, in any suitable computer-based system. Processor 240 may be configured to execute instructions stored on a tangible, non-transitory computer readable medium, causing processor 240 to perform various operations. In various embodiments, processor 240 may also include any combination of processing circuits known in the art, such as one or more microprocessors, microcontrollers, digital signal processors, and/or programmable logic devices. Processor 240 may be in logical and/or electronic communication with fuel control actuator 230, fuel temperature sensor 250, fuel filter pressure sensor 255, and/or FLI database 260. Processor 240 may be in logical and/or electronic communication using any method disclosed herein or known in the art, such as, for example, via wiring or radio frequency transmissions.

In various embodiments, processor 240 may be configured to electronically control fuel control actuator 230. Processor 240 may electronically control fuel control actuator 230 to control the flow of fuel through fuel system 200. In this regard, processor 240 may be in logical and/or electronic communication with fuel control actuator 230. Processor 240 may be in logical and/or electronic communication using any method disclosed herein or known in the art, such as, for example, via wiring or radio frequency transmissions.

In various embodiments, fuel temperature sensor 250 may be configured to monitor the temperature of the fuel in fuel system 200. Fuel temperature sensor 250 may be configured to monitor the temperature of the fuel and send the measured temperature data, via processor 240, to FLI database 260 for storage. Fuel temperature sensor 250 may comprise any suitable type of sensor, probe, and/or the like capable of monitoring the temperature of a liquid (such as a fuel). Fuel temperature sensor 250 may be configured to monitor the temperature of the fuel at any suitable and/or desired location. For example, fuel temperature sensor 250 may be configured to monitor the temperature of the fuel in fuel tank 210. In this regard, fuel temperature sensor 250 may be located in close proximity to fuel tank 210 or in fuel tank 210. Fuel temperature sensor 250 may also be configured to monitor the temperature of the fuel at a point downstream of fuel tank 210, such as at a fuel pipe between fuel tank 210 and fuel filter 220. In this regard, fuel temperature sensor 250 may be located in close proximity to the fuel pipe or in the fuel pipe. Fuel temperature sensor 250 may be in logical and/or electronic communication with processor 240. Fuel temperature sensor 250 may be in logical and/or electronic communication using any method disclosed herein or known in the art, such as, for example, via wiring or radio frequency transmissions.

In various embodiments, fuel filter pressure sensor 255 may be configured to monitor the differential pressure across fuel filter 220. Fuel filter pressure sensor 255 may be configured to monitor the fuel filter differential pressure at periodic intervals, determine the highest measured fuel filter differential pressure, and send the highest measured fuel filter differential pressure, via processor 240, to FLI database 260 for storage. Fuel filter pressure sensor 255 may comprise any suitable type of sensor, probe, and/or the like capable of monitoring the pressure of the fuel in fuel filter 220. Fuel filter pressure sensor 255 may be located in any location suitable to monitor the differential pressure across fuel filter 220. In this regard, fuel filter pressure sensor 255 may be located in close proximity to fuel filter 220. In various embodiments, fuel filter pressure sensor 255 may monitor the pressure at two locations, on either side of fuel filter 220. Processor 240 may then calculate the differential pressure by taking the difference of the pressure measurements from each location of measurement. Fuel filter pressure sensor 255 may be in logical and/or electronic communication with processor 240. Fuel filter pressure sensor 255 may be in logical and/or electronic communication using any method disclosed herein or known in the art, such as, for example, via wiring or radio frequency transmissions.

In various embodiments, FLI database 260 may be configured to store and maintain data. FLI database 260 may be configured to store and maintain any data relating to the calculation of the fuel lacquer index, and/or related to the health monitoring of fuel system 200. FLI database 260 may store and maintain data using any suitable method disclosed herein or known in the art. FLI database 260 may be in logical and/or electronic communication with processor 240. FLI database 260 may be in logical and/or electronic communication using any method disclosed herein or known in the art, such as, for example, via wiring or radio frequency transmissions.

Figure 3:
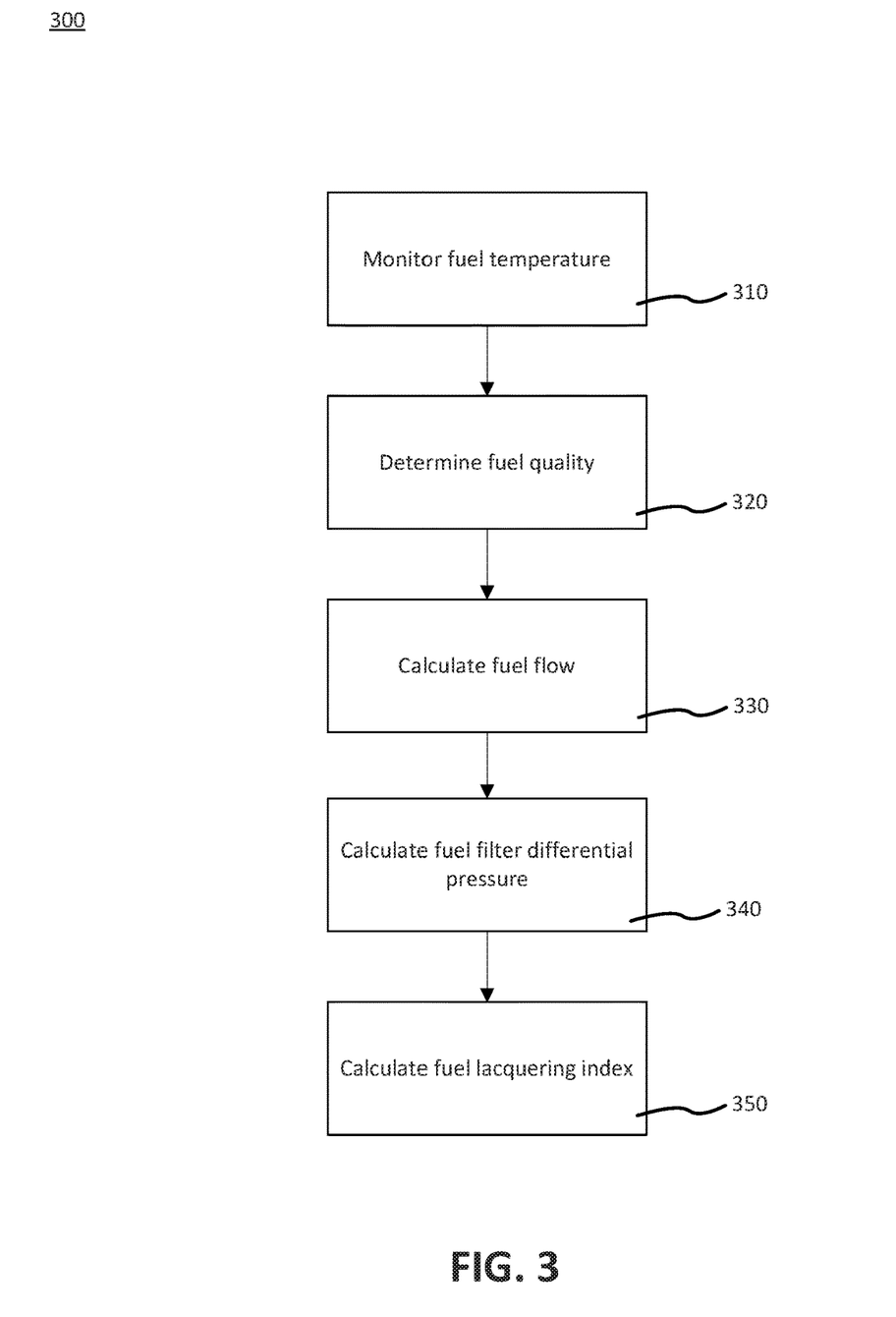
FIG. 3 illustrates a flow chart of a method for calculating a fuel lacquer index, in accordance with various embodiments.

In various embodiments, with reference to FIG. 3 and further reference to FIG. 2, a method 300 for the calculation of a fuel lacquer index using environmental monitoring is disclosed. The fuel lacquer index may comprise a value, for example, ranging from 0% to 100%, intended to provide an estimated value of the amount that a fuel system component may be blocked or clogged by fuel lacquering particulate. For example, the fuel lacquer index of 100% in a fuel system component may represent that the fuel system component is about 100% blocked by particulate due to fuel lacquering. In that regard, a 100% blocked fuel system is not able to conduct fluid flow. A fuel lacquer index of 50% may represent that the fuel system component is about 50% blocked by particulate due to fuel lacquering. Thus, the fuel lacquer index may provide an indication of the overall health of a fuel system component, by indicating the percent, or value, that the fuel system component has been blocked by particulate due to fuel lacquering. In various embodiments, method 300 may monitor and trend environmental factors present in a fuel system, in order to determine the fuel lacquer index.

In various embodiments, method 300 may comprise monitoring the fuel temperature (step 310). The rate at which fuel lacquering occurs may increase as fuel temperature rises. Moreover, operating conditions conducive to fuel lacquering may be expected to occur at temperatures greater than 230° F. In this regard, the fuel temperature may therefore be a factor in determining the fuel lacquer index.

In various embodiments, step 310 may comprise capturing fuel temperature data. The fuel temperature data may comprise the temperature of the fuel captured by fuel temperature sensor 250 during the time of the measurement. Processor 240 may be configured to communicate with fuel temperature sensor 250 to capture the fuel temperature data. Processor 240 may also be configured to capture the time at which the fuel temperature data was taken. In this regard, fuel temperature sensor 250 may set a desired starting point (e.g., a time 0), and measure the time period that the fuel temperature data is at a particular temperature reading. For example, fuel temperature sensor 250 may return the fuel temperature data of 225° F. beginning at the time 0. If the fuel temperature data remains at 225° F. for subsequent measurements during the next 10 minutes, before then returning the fuel temperature data of 240° F., the time of the fuel temperature data may be 10 minutes (or 600 seconds, and/or any other suitable time measurement value).

In various embodiments, processor 240 may also be configured to communicate with fuel temperature sensor 250 to capture the fuel temperature data at a fixed time interval. The fixed time interval may comprise the interval of time that processor 240 may wait until monitoring fuel temperature sensor 250 to measure the fuel temperature data. The fixed time interval may comprise any suitable and/or desired interval of time for measurements. For example, and in various embodiments, the fixed time interval may be 60 seconds (e.g., processor 240 monitors fuel temperature sensor 250 every 60 seconds). The fixed time interval may also comprise 30 seconds (e.g., processor 240 monitors fuel temperature sensor 250 every 30 seconds), 5 minutes (e.g., processor 240 monitors fuel temperature sensor 250 every 5 minutes), and/or any other desired time interval. The processor 240 may use the same initial time (e.g., time 0) in capturing both fuel temperature data and the fuel filter differential pressure. In this regard, a fuel temperature may be associated with a fuel pressure at the same time. Such data may be stored in FLI database 260.

In various embodiments, step 310 may further comprise storing the fuel temperature data in FLI database 260. In this regard, processor 240 may receive the fuel temperature data from fuel temperature sensor 250, and transmit the reading to FLI database 260. FLI database 260 may receive and store the fuel temperature data using any suitable method described herein or known in the art.

In various embodiments, FLI database 260 may be configured to store the fuel temperature data in datasets grouped by temperature range. For example, FLI database 260 may store all the fuel temperature data from a temperature range of 180° F. to 200° F. in "dataset1," all the fuel temperature data from a temperature range of 200° F. to 220° F. in "dataset2," and so forth. A dataset may correspond to any suitable and/or desired temperature range. Datasets may be implemented in various relational databases, delimited text files, and/or other suitable information storage and retrieval systems. In various embodiments, processor 240 may also simultaneously transmit and store the fuel filter differential pressure and volumetric fuel flow measurements that were measured at the same time interval as the fuel temperature data. In this regard, the fuel temperature data, the fuel filter differential pressure, and the volumetric fuel flow measured during the same time interval may be grouped and stored together, in the appropriate dataset in FLI database 260.

In various embodiments, processor 240 may also be configured to transmit the time at the fuel temperature data to FLI database 260. FLI database 260 may store the time of the fuel temperature data in each corresponding dataset, matched up with the fuel temperature data that was measured simultaneously as the time at the fuel temperature data. By storing the time at fuel temperature data for each dataset, processor 240 may calculate the total time that the fuel in fuel system 200 was at the temperature range associated with each individual dataset.

In various embodiments, method 300 may comprise determining the quality of the fuel in the fuel system (step 320). The quality of the fuel used in the fuel system may contribute to fuel lacquering. As the amount of catalysts, contaminants, and dissolved oxygen in the fuel increases, and the quality of the fuel likewise decreases, fuel lacquering may also increase. Therefore, the quality of the fuel in the fuel system may also be a factor in determining the fuel lacquer index.

In various embodiments, the quality of the fuel in the fuel system may be measured using any suitable means discussed herein and/or known in the art. The quality of the fuel may be calculated as a fuel quality rating. In various embodiments, the fuel quality rating may be inferred from the location at which the aircraft last filled its fuel tanks. In this regard, known locations of refueling stations may be tested for the quality of the fuel present. The fuel at a refueling station may be tested using any suitable method known in the art. The location of the refueling station, along with the fuel quality rating associated with fuel dispensed at the refueling station, may then be stored in a database, such as FLI database 260. Thus, upon refueling at a particular refueling station, the fuel quality rating associated with that particular refueling station may be found in, and retrieve from, FLI database 260.

In various embodiments, the fuel quality rating may comprise a qualitative rating such as a low fuel quality rating, a medium fuel quality rating, and/or a high fuel quality rating. The fuel quality rating may also comprise any other suitable qualitative rating or scale. Each qualitative rating may comprise any number of factors and ranges to determine whether the tested fuel falls within the fuel quality rating. For example, the qualitative rating may relate to the amount of contaminants present in the tested fuel. Some common fuel contaminants known to impart fuel lacquering may include "heteroatoms" such as oxygen, nitrogen, or sulfur-containing species, and/or metal catalysts. The fuel quality rating may therefore not only take into account the quantity of contaminants present in the tested fuel, but also the type of contaminants present in the tested fuel (e.g., some types of contaminants may have a higher effect on fuel lacquering compared to other types of contaminants).

In various embodiments, a low fuel quality rating may comprise fuel that has a high level of contaminants. The low fuel quality rating may comprise any suitable range of contaminants considered to be a "high level." For example, a low fuel quality rating may comprise fuel that has a level of contaminants considered to have a high impact on fuel lacquering. A medium fuel quality rating may comprise fuel that has a medium level of contaminants. The medium fuel quality rating may comprise any suitable range of contaminants considered to be a "medium level." For example, a medium fuel quality rating may comprise fuel that has a level of contaminants considered to have a medium impact on fuel lacquering. A high fuel quality rating may comprise fuel that has a low level of contaminants. The high fuel quality rating may comprise any suitable range of contaminants considered to be a "low level." For example, a high fuel quality rating may comprise fuel that has a level of contaminants considered to have a low and/or negligible effect on fuel lacquering.

In various embodiments, method 300 may comprise calculating a volumetric fuel flow (step 330). The volumetric fuel flow in fuel system 200 may be a factor contributing to fuel lacquering in a fuel system. The volumetric fuel flow may comprise a measurement of the volume of fuel passing through a fuel system component (such as, for example, fuel control actuator 230) per unit time. As the rate of fuel flow through a component increases, the amount of particulates deposited from fuel lacquering may also increase. Therefore, volumetric fuel flow may also be a factor in determining the fuel lacquer index.

In various embodiments, the volumetric fuel flow may be calculated and/or captured using any suitable method discussed herein or known in the art. For example, the volumetric fuel flow may be dependent on fuel control actuator 230 movement. In this regard, the volumetric fuel flow through fuel control actuator 230 may be calculated, by processor 240, based on volumetric fuel flow models. For example, volumetric fuel flow models may be used to predict the volumetric fuel flow when fuel control actuator 230 is not moving, fully extended, and/or fully retracted. In this regard, various parameters may be used in the volumetric fuel flow models to predict the volumetric fuel flow. For example, if fuel control actuator 230 is not moving, volumetric fuel flow may be estimated based on a function of a fuel flow rate multiplied by an amount of time monitored. The fuel flow rate may be inferred using the fuel filter differential pressure captured by fuel filter pressure sensor 255. As a further example, if fuel control actuator 230 is extending, the volumetric fuel flow model may correct for the fuel displaced by the movement of fuel control actuator 230. It should be understood that any suitable model and/or method of measuring the volumetric fuel flow may be used in the present disclosure. In various embodiments, processor 240 may be configured to transmit the volumetric fuel flow to FLI database 260.

In various embodiments, method 300 may comprise calculating a fuel filter differential pressure (step 340). The fuel filter differential pressure may be an environmental factor contributing to fuel lacquering in a fuel system. An increase in fuel filter differential pressure over time may indicate the potential occurrence of fuel lacquering. As such, the fuel filter differential pressure may also be a factor for the calculation of the fuel lacquer index.

In various embodiments, the fuel filter differential pressure may be calculated by processor 240. Processor 240 may communicate with fuel filter pressure sensor 255 to receive the fuel filter differential pressure. Processor 240 may be configured to communicate with fuel filter pressure sensor 255 at various time intervals to gather the fuel filter differential pressure. As discussed above, processor 240 may be configured to calculate the fuel filter differential pressure at the same time interval as the fuel temperature data, such that the two factors may be calculated and stored simultaneously. Processor 240 may be configured to transmit the fuel filter differential pressure to FLI database 260 for storage. In various embodiments, processor 240 may be configured to store only the maximum value of the fuel filter differential pressure calculated during aircraft flight.

In various embodiments, method 300 may comprise calculating a fuel lacquer index (step 350). The fuel lacquer index may comprise a value that ranges from 0%-100%, representing an approximate percentage that a fuel system component may be blocked due to fuel lacquering. The fuel lacquer index may also comprise an integer, a real number between 0 and 1, and/or any other suitable measurement capable of representing the approximate blockage of the fuel system component due to fuel lacquering. For example, a high percentage value in the fuel lacquer index may relate to a fuel system component (such as, for example, a fuel system screen or a fuel system actuator) that is inundated with particulate from fuel lacquering. Similarly, a low percentage value in the fuel lacquer index may relate to a fuel system component that may have some clogging from particulate caused by fuel lacquering (however small an amount). In various embodiments, the calculation of the fuel lacquer index may be used to mitigate the risk of associated fuel system component failures. In this regard, the fuel lacquer index may provide an early warning of a potential problem with a fuel system component.

In various embodiments, the fuel lacquer index may be calculated by processor 240. The fuel lacquer index may comprise a function of various environmental factors that may be causes of fuel lacquering. By gathering data known to contribute to fuel lacquering, the data may be trended and analyzed to determine the fuel lacquering occurring in fuel system 200. For example, the fuel lacquer index may comprise a function of the fuel temperature data, the fuel quality rating, the volumetric fuel flow, and the fuel filter differential pressure. Processor 240 may communicate with FLI database 260 to retrieve the fuel temperature data, the fuel quality rating, the volumetric fuel flow, and the fuel filter differential pressure. The history and prior measurements of those environmental factors, stored in and retrieved from FLI database 260, may be trended and analyzed by processor 240 to calculate the fuel lacquer index. For example, the environmental factors may be compared to a fuel lacquer index model, wherein the fuel temperature data, the volumetric fuel flow, and the fuel filter differential pressure may be compared to prior measurements where the resulting fuel lacquering was known, and the fuel lacquer index may be calculated based upon the amount of time measured at those data points.

In various embodiments, processor 240 may calculate the fuel lacquer index, and transmit the fuel lacquer index to FLI database 260 for storage. At the end of every aircraft flight, or at any other suitable and/or desired time interval, processor 240 may also recalculate a new (second) fuel lacquer index and add the new (second) fuel lacquer index to the stored (first) fuel lacquer index.

Figure 4:
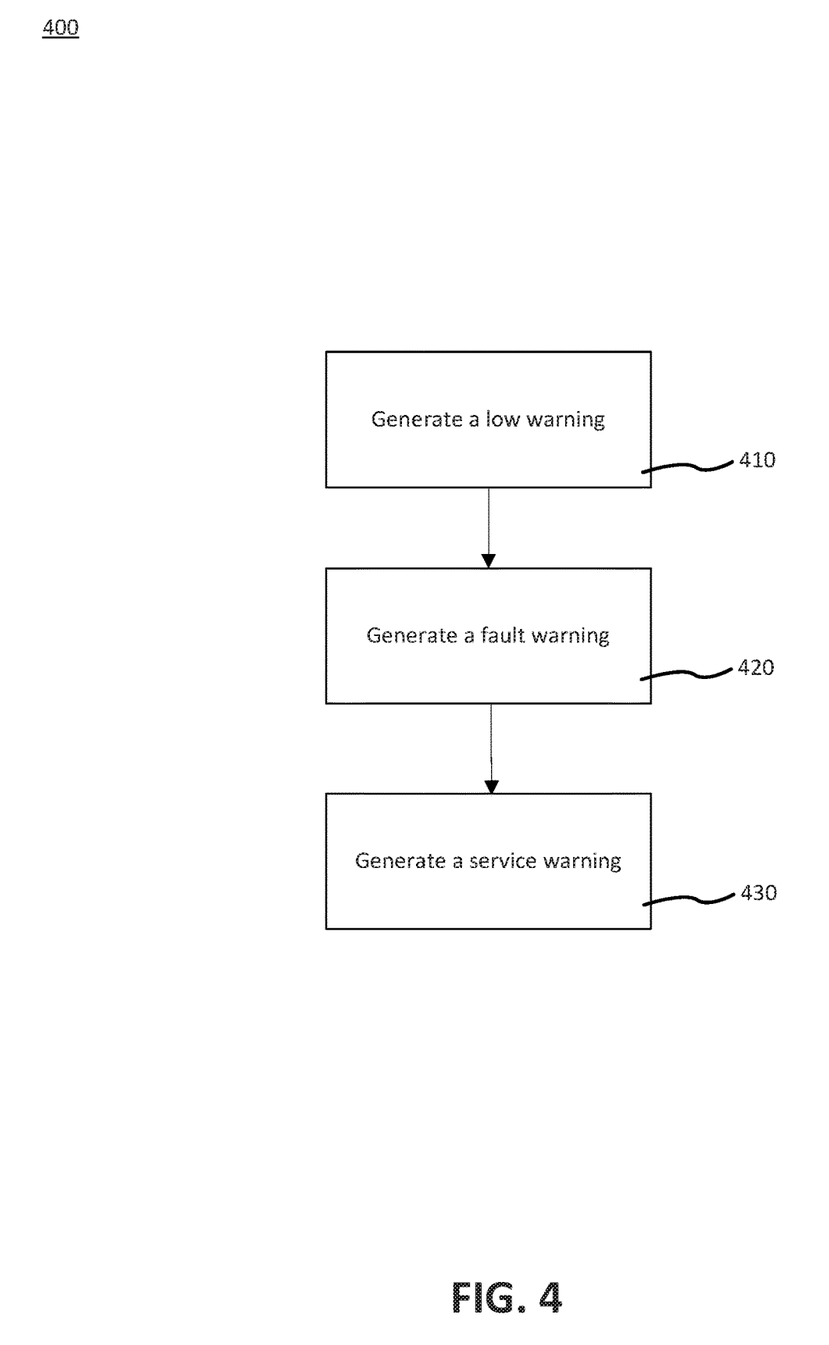
FIG. 4 illustrates a flow chart of a method of alerting based on the fuel lacquer index, in accordance with various embodiments.

In various embodiments, with reference to FIG. 4 and further reference to FIG. 2, a method 400 for the generation of warnings based on the fuel lacquer index is disclosed. In various embodiments, method 400 may comprise generating a low warning based on the fuel lacquer index (step 410). The low warning may be generated by processor 240. Processor 240 may be configured to generate the low warning when the fuel lacquer index reaches a defined threshold. For example, the low warning may be generated to alert that a fuel system component has been blocked by particulate from fuel lacquering, but is not yet so blocked that the fuel system component may fail. In various embodiments, the defined threshold may be set to any desired level. In this regard, the defined threshold may be set to 50%, 60%, and/or any other suitable value. The low warning may be transmitted, by processor 240, to a health monitoring system, a flight management system, fleet monitoring, and/or any other suitable system.

In various embodiments, method 400 may comprise generating a fault warning based on the fuel lacquer index (step 420). The fault warning may be generated by processor 240. Processor 240 may be configured to generate the fault warning when the fuel lacquer index reaches a defined threshold. For example, the fault warning may be generated to alert that a fuel system component has been clogged by particulate from fuel lacquering to a level that may benefit from servicing. In various embodiments, the defined threshold may be set to any desired level. In this regard, the defined threshold may be set to 65%, 70%, 75%, and/or any other suitable value. The fault warning may be transmitted, by processor 240, to a health monitoring system, a flight management system, fleet monitoring, and/or any other suitable system.

In various embodiments, method 400 may comprise generating a service warning based on the fuel lacquer index (step 430). The service warning may be generated by processor 240. Processor 240 may be configured to generate the service warning when the fuel lacquer index reaches a defined threshold. For example, the service warning may be generated to alert that a fuel system component has been compromised by particulate from fuel lacquering, such that the fuel system component may imminently fail. As such, the service warning may be used to alert that a fuel system component may benefit from immediate servicing. In various embodiments, the defined threshold may be set to any desired level. In this regard, the defined threshold may be set to 80% 85%, 90%, and/or any other suitable value. The service warning may be transmitted, by processor 240, to a health monitoring system, a flight management system, fleet monitoring, and/or any other suitable system.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosures. The scope of the disclosures is accordingly to be limited by nothing other than the appended claims and their legal equivalents, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method, comprising:
   capturing, by a processor and via a fuel temperature sensor, a fuel temperature data;
   determining, by the processor, a fuel quality;
   calculating, by the processor and via a fuel control actuator, a volumetric fuel flow;
   calculating, by the processor and via a fuel filter pressure sensor, a fuel filter differential pressure;
   calculating, by the processor, a fuel lacquer index by comparing the fuel temperature data, the fuel quality rating, the volumetric fuel flow, and the fuel filter differential pressure to a fuel lacquer index model comprising historical data points and known resulting fuel lacquering, wherein the fuel lacquer index comprises an estimated amount that a fuel system component is blocked or clogged by a fuel lacquering particulate; and
   generating, by the processor, a warning based on the fuel lacquer index, wherein based on the warning the fuel system component is at least one of serviced or replaced with a second fuel system component.

2. The method of claim 1, further comprising generating, by the processor, a low warning in response to the fuel lacquer index being greater than 60%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

3. The method of claim 1, further comprising generating, by the processor, a fault warning in response to the fuel lacquer index being greater than 75%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

4. The method of claim 1, further comprising generating, by the processor, a service warning in response to the fuel lacquer index being greater than 85%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

5. The method of claim 1, wherein the fuel temperature data, the fuel quality rating, the volumetric fuel flow, and the fuel filter differential pressure are stored in a fuel lacquer index ("FLI") database, wherein the FLI database is in electronic communication with the processor.

6. The method of claim 1, wherein the fuel quality rating comprises at least one of a low fuel quality rating, a medium fuel quality rating, or a high fuel quality rating.

7. The method of claim 1, wherein the volumetric fuel flow is calculated through the use of a volumetric fuel flow model, wherein the volumetric fuel flow model is based upon a position of the fuel control actuator.

8. A system, comprising:
a fuel temperature sensor configured to monitor a temperature of a fuel;
a fuel control actuator configured to control fuel flow;
a fuel filter pressure sensor configured to monitor a pressure differential across a fuel filter; and
a processor in electronic communication with the fuel temperature sensor, the fuel control actuator, and the fuel filter pressure sensor, wherein the processor is configured to perform operations comprising:
capturing, by the processor and via the fuel temperature sensor, a fuel temperature data;
determining, by the processor, a fuel quality rating;
calculating, by the processor and via the fuel control actuator, a volumetric fuel flow;
calculating, by the processor and via the fuel filter pressure sensor, a fuel filter differential pressure;
calculating, by the processor, a fuel lacquer index by comparing the fuel temperature data, the fuel quality rating, the volumetric fuel flow, and the fuel filter differential pressure to a fuel lacquer index model comprising historical data points and known resulting fuel lacquering, wherein the fuel lacquer index comprises an estimated amount that a fuel system component is blocked or clogged by a fuel lacquering particulate; and
generating, by the processor, a warning based on the fuel lacquer index, wherein based on the warning the fuel system component is at least one of serviced or replaced with a second fuel system component.

9. The system of claim 8, wherein the operations further comprise generating, by the processor, a low warning in response to the fuel lacquer index being greater than 60%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

10. The system of claim 8, wherein the operations further comprise generating, by the processor, a fault warning in response to the fuel lacquer index being greater than 75%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

11. The system of claim 8, wherein the operations further comprise generating, by the processor, a service warning in response to the fuel lacquer index being greater than 85%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

12. The system of claim 8, wherein the fuel temperature data, the fuel quality rating, the volumetric fuel flow, and the fuel filter differential pressure are stored in a FLI database, wherein the FLI database is in electronic communication with the processor.

13. The system of claim 8, wherein the fuel quality rating comprises at least one of a low fuel quality rating, a medium fuel quality rating, or a high fuel quality rating.

14. The system of claim 8, wherein the volumetric fuel flow is calculated through the use of a volumetric fuel flow model, and wherein the volumetric fuel flow model is based upon a position of the fuel control actuator.

15. An article of manufacture including a tangible, non-transitory computer-readable storage medium having instructions stored thereon that, in response to execution by a processor, cause the processor to perform operations comprising:
capturing, by the processor, a fuel temperature data;
determining, by the processor, a fuel quality rating;
calculating, by the processor, a volumetric fuel flow;
calculating, by the processor, a fuel filter differential pressure;
calculating, by the processor, a fuel lacquer index by comparing the fuel temperature data, the fuel quality rating, the volumetric fuel flow, and the fuel filter differential pressure to a fuel lacquer index model comprising historical data points and known resulting fuel lacquering, wherein the fuel lacquer index comprises an estimated amount that a fuel system component is blocked or clogged by a fuel lacquering particulate; and
generating, by the processor, a warning based on the fuel lacquer index, wherein based on the warning the fuel system component is at least one of serviced or replaced with a second fuel system component.

16. The article of manufacture of claim 15, wherein the operations further comprise generating, by the processor, a low warning in response to the fuel lacquer index being greater than 60%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

17. The article of manufacture of claim 15, wherein the operations further comprise generating, by the processor, a fault warning in response to the fuel lacquer index being greater than 75%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

18. The article of manufacture of claim 15, wherein the operations further comprise generating, by the processor, a service warning in response to the fuel lacquer index being greater than 85%, wherein the fuel lacquer index of 0% represents the fuel system component being unblocked or unclogged by the fuel lacquering particulate, and wherein the fuel lacquer index of 100% represents the fuel system component being completely blocked or clogged by the fuel lacquering particulate.

19. The article of manufacture of claim 15, wherein the fuel temperature data, the fuel quality rating, the volumetric fuel flow, and the fuel filter differential pressure are stored in a FLI database, wherein the FLI database is in electronic communication with the processor.

20. The article of manufacture of claim 15, wherein the fuel quality rating comprises one of a low fuel quality rating, a medium fuel quality rating, or a high fuel quality rating.

* * * * *